United States Patent
Morris, Sr. et al.

(10) Patent No.: US 9,332,927 B2
(45) Date of Patent: May 10, 2016

(54) FLUID HEAT TRANSFER SYSTEM FOR ANIMAL DIAGNOSTIC BED AND METHODS OF USING THE SAME

(71) Applicant: SA INSTRUMENTS, INC., Ft. Lauderdale, FL (US)

(72) Inventors: George Ronald Morris, Sr., Ft. Lauderdale, FL (US); Douglas Fox Tomlinson, Waunakee, WI (US)

(73) Assignee: SA Instruments, Inc., Ft. Lauderdale, FL (US)

( * ) Notice: Subject to any disclaimer, the term of this patent is extended or adjusted under 35 U.S.C. 154(b) by 220 days.

(21) Appl. No.: 14/198,170

(22) Filed: Mar. 5, 2014

(65) Prior Publication Data

US 2014/0257082 A1    Sep. 11, 2014

Related U.S. Application Data

(60) Provisional application No. 61/772,724, filed on Mar. 5, 2013.

(51) Int. Cl.
*A61B 5/05*    (2006.01)
*A61B 5/055*    (2006.01)

(52) U.S. Cl.
CPC .................. *A61B 5/0555* (2013.01)

(58) Field of Classification Search
CPC ........ A61B 5/5555; A61B 5/055; A61B 5/05; A61B 5/01; A61B 5/015; A61B 5/555
USPC .................................................. 600/407–430
See application file for complete search history.

(56) References Cited

U.S. PATENT DOCUMENTS

| | | | |
|---|---|---|---|
| 6,066,087 A * | 5/2000 | Tron | A61H 33/06 600/21 |
| 8,181,290 B2 | 5/2012 | Brykalski et al. | |
| 8,418,286 B2 | 4/2013 | Brykalski et al. | |
| 2005/0251914 A1* | 11/2005 | Schaller | A61B 5/0555 5/601 |
| 2010/0101500 A1* | 4/2010 | Sannie | A61D 7/04 119/420 |
| 2011/0224536 A1* | 9/2011 | Pile-Spellman | A61B 5/01 600/412 |

* cited by examiner

*Primary Examiner* — Sanjay Cattungal
(74) *Attorney, Agent, or Firm* — Amster, Rothstein & Ebenstein, LLP

(57) ABSTRACT

A diagnostic system is disclosed, and comprises a diagnostic device and a fluid heat transfer system. The diagnostic device has an associated bed for supporting a portion of a subject during a diagnostic procedure. The fluid heat transfer system comprises a fluid circulation component, a heater component, and a fluid line. The heater component includes a heater element and a mixing valve, and the fluid circulation component is fluidly coupled to the heater component so that a fluid can be pumped from the fluid circulation component to the heater component. The fluid line extends from the heater to the fluid circulation component, and the mixing valve is positioned near the bed so that heat can be rapidly transferred through the fluid line to alter a body temperature of the subject.

16 Claims, 7 Drawing Sheets

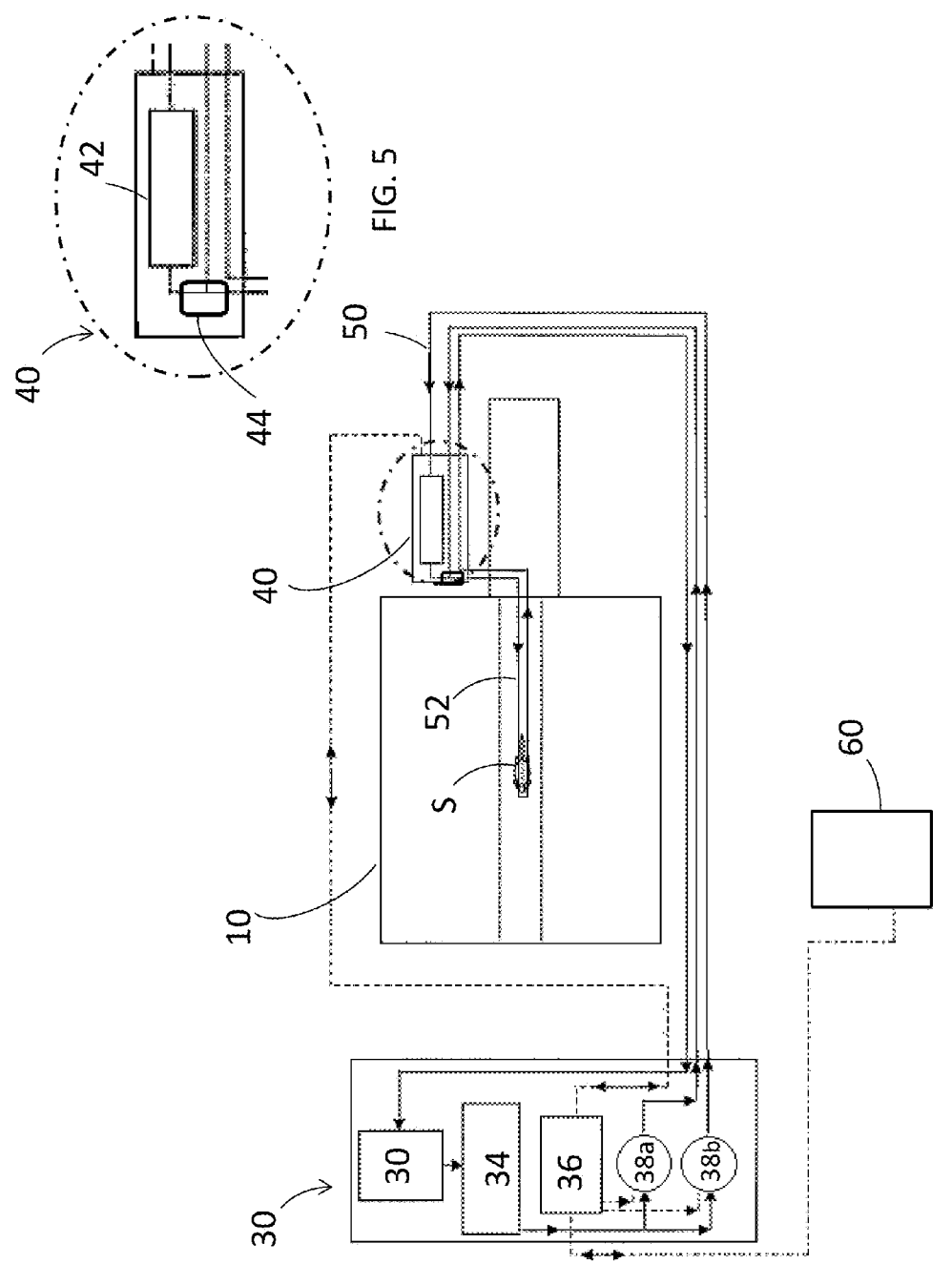

FLUID HEAT TRANSFER SYSTEM FOR ANIMAL DIAGNOSTIC BED AND METHODS OF USING THE SAME

CROSS-REFERENCE TO RELATED APPLICATION

The present application claims priority to and the benefit of U.S. Provisional Patent Application No. 61/772,724, filed on Mar. 5, 2013, the entire contents of which are incorporated by reference herein.

FIELD OF INVENTION

The present invention generally relates to a fluid heat transfer system for use with a bed so that a body temperature of the subject on the bed can be controlled. In exemplary embodiments, the present invention generally relates to a bed supporting a body of a subject during a diagnostic procedure, and includes a fluid heat transfer system to regulate a body temperature of the subject disposed on the bed during the diagnostic procedure.

BACKGROUND

In the course of performing diagnostic procedures, for example, gathering optical, thermal, electromagnetic, and/or other physical measurements or characteristics of a body of a subject, to name a few, it may be desirable to maintain a body temperature of the subject above or below a threshold value or within a desired range. Such diagnostic procedures may be used to diagnose, treat, and/or monitor a subject in conjunction with, for example, medical testing, medical treatment, medical research, and/or scientific research, to name a few.

For example, in the field of medical research, several physiological parameters are affected by a subject's body temperature, for example, respiration rate, blood pressure, and blood oxygen saturation, to name a few. Further, some substances being researched for use in treating illnesses have been found to have an effectiveness associated with a body temperature of a subject to which they are applied.

As another example, medical scanning equipment such as magnetic resonance imaging (MRI) may produce heat in the body of a subject during use, such that a body temperature of the subject fluctuates across duty cycles of the MRI scanner. Such problems with variable body temperature of a subject may be compounded where the body mass of the subject is relatively small, for example, in rodents such as lab rats or mice used for medical testing, so that the change in the body temperature of the subject can change rapidly and/or between extreme values.

Accordingly, it would be desirable to provide a system for regulating a body temperature of a subject during the course of a diagnostic procedure. It would be further desirable to adapt such a system for integration into currently-available diagnostic devices so that a substantial reconfiguration of existing architecture is not required to achieve effective regulation of the body temperature of a subject.

SUMMARY

According to an exemplary embodiment of the present invention, a diagnostic system is disclosed, and comprises a diagnostic device and a fluid heat transfer system. The diagnostic device has an associated bed for supporting a portion of a subject during a diagnostic procedure. The fluid heat transfer system comprises a fluid circulation component, a heater component, and a fluid line. The heater component includes a heater element and a mixing valve, and the fluid circulation component is fluidly coupled to the heater component so that a fluid can be pumped from the fluid circulation component to the heater component. The fluid line extends from the heater to the fluid circulation component, and the mixing valve is positioned near the bed so that heat can be rapidly transferred through the fluid line to alter a body temperature of the subject.

In an exemplary embodiment, the mixing valve comprises an inlet for the fluid at a first temperature and an inlet for the fluid at a second, higher temperature.

In an exemplary embodiment, the mixing valve comprises an outlet for the fluid at a temperature intermediate the first temperature and second temperature.

In an exemplary embodiment, the bed comprises a frame and a plurality of protrusions extending therefrom.

In an exemplary embodiment, the fluid line is configured to interengage one or more protrusion of the plurality of protrusions to maintain the fluid line in position near the bed.

In an exemplary embodiment, the diagnostic device is an MRI device.

In an exemplary embodiment, the fluid circulation component comprises a pump.

In an exemplary embodiment, the diagnostic system further comprises a control interface electrically coupled with one or more of fluid circulation component and heater component.

In an exemplary embodiment, the control interface is electrically coupled with the mixing valve.

In an exemplary embodiment, the control interface can cause a flow rate through one of a first inlet and a second inlet of the mixing valve to change.

According to an exemplary embodiment of the present invention, a diagnostic system comprises a bed or supporting a portion of a subject during a diagnostic procedure and a fluid heat transfer system. The fluid heat transfer system comprises a first fluid line fluidly coupled with a heating element, a second fluid line, a mixing valve, and a third fluid line. The mixing valve is disposed downstream of the heating element and has a first fluid inlet corresponding to the first fluid line and a second fluid inlet corresponding to the second fluid line. The mixing valve further includes an outlet for a mixed fluid having a temperature higher than a temperature of fluid in the second fluid line. The third fluid line extends away from the mixing valve, and is positioned near the bed such that the mixed fluid rapidly transfers heat from the third fluid line to a subject on the bed.

In an exemplary embodiment, a first fluid pump is fluidly coupled with the first fluid line.

In an exemplary embodiment, a second fluid pump is fluidly coupled with the second fluid line.

In an exemplary embodiment, the diagnostic system further comprises a controller operably coupled with each of the first fluid pump and the second fluid pump.

In an exemplary embodiment, the diagnostic system further comprises a controller operably coupled with the heating element.

In an exemplary embodiment, a thermal sensor is disposed downstream of the mixing valve and electrically coupled with the controller such that the controller controls the transfer of heat from the heating element into fluid therealong.

In an exemplary embodiment, another thermal sensor is disposed upstream of the mixing valve and in electrical communication with the controller so that the controller can determine a difference in the temperature at the thermal sensor with the temperature at the another thermal sensor.

BRIEF DESCRIPTION OF DRAWINGS

Various exemplary embodiments of this invention will be described in detail, with reference to the following figures, wherein:

FIG. 4 is a schematic view of the diagnostic system of FIG. 1;

FIG. 5 is an enlarged view of the area of detail identified in FIG. 4;

DETAILED DESCRIPTION

Embodiments described herein are generally directed toward beds and/or other supporting surfaces that incorporate a fluid heat transfer system to regulate a body temperature of a subject disposed on the bed during a diagnostic procedure. In this manner, a user can control the body temperature of the subject. The body temperature can be maintained within a desired value or range so that one or more diagnostic procedures can be performed in an at least partially controlled environment.

As described herein, the term "bed" may refer to any bed, platform, and/or surface for supporting at least a portion of a subject's body during a diagnostic procedure. As described herein, the terms "diagnostic device" and "diagnostic procedure," respectively, may refer to any device and associated method of use thereof for gathering physiological information associated with the body of a subject, as described further herein. It will be understood that the systems for regulating a body temperature of a subject according to exemplary embodiments described herein may be used in additional or alternative scenarios where a body temperature of a subject is sought to be regulated, for example, medical, surgical, and/or other treatment or recovery procedures.

Figure 1:
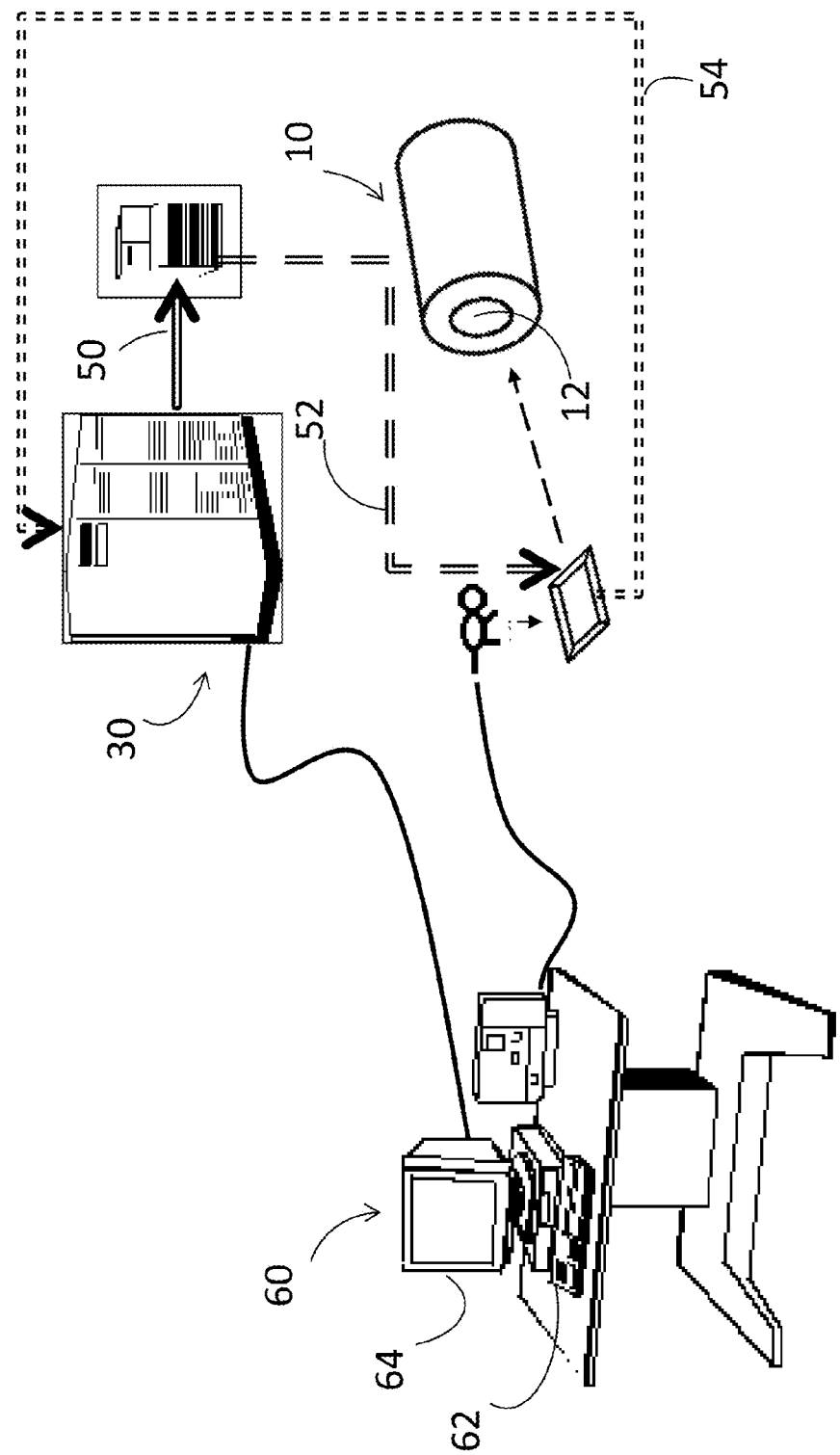
FIG. 1 is a perspective view of a diagnostic system according to an exemplary embodiment of the present disclosure.

Turning to FIG. 1, an exemplary embodiment of a diagnostic system is generally designated 100, and includes a diagnostic device 10 with a diagnostic bed 20 for supporting at least a portion of a body of a subject S. Diagnostic bed 20 may be movable relative to diagnostic device 10, for example, diagnostic bed 20 may be movable into and out of a bore 12 defined at least partially through the diagnostic device 10. In the exemplary embodiment shown, subject S may be a small animal such as a rodent and diagnostic device 10 may be a magnetic resonance imaging (MRI) device. In embodiments, subject S may be a different animal, for example, a canine or human, and diagnostic device 10 may be a different diagnostic device, for example, a computerized tomography (CT) scanner, a positron emission tomography (PET) scanner, an ultrasound scanner, a thermal imaging scanner, an X-ray scanner, or a bioelectrical feedback detectors such as a dermal electrode, to name a few.

Diagnostic system 100 incorporates a fluid heat transfer system that is configured to circulate at least one fluid through or near the diagnostic bed 20 such that heat can be transferred between the fluid and the body of the subject S to regulate a body temperature of the subject S. In embodiments, the fluid may be a liquid such as water. In embodiments, the fluid may be a gas such as air. It will be understood by those skilled in the art of the present disclosure that a variety of fluids may be used with the diagnostic system of the present disclosure, and that such fluid can be chosen based on its material properties to achieve a desired result.

Accordingly, the heat transfer system of diagnostic system 100 comprises a fluid circulation component 30 and a heater component 40 fluidly coupled by a fluid delivery line 50 so that fluids from the circulation component 30 can be pumped toward the heater component 40. A fluid return line 52 extends away from the heater component 40 and provides a return path for the fluid to the circulation component 30 such that a closed fluid system is formed. In embodiments, fluids may flow through the fluid heat transfer system of diagnostic system 100 along multiple fluid lines in any combination or separation thereof, or may flow along a single unitarily constructed fluid line.

The fluid circulation component 30 of diagnostic system 100 is configured to apply pressure to fluid through the fluid lines 50, 52 toward diagnostic bed 20. The heater component 40 is in fluid communication between fluid circulation component 30 and diagnostic bed 20, and is configured to apply heat to the fluid as it passes therethrough. The fluid then passes from the heater component 40 through fluid return line 52 that extends near or along the diagnostic bed 20 so that heat stored in the fluid traveling therethrough can be transferred to the subject S disposed on the diagnostic bed 20. Fluid then travels away from the diagnostic bed 20 along the fluid return line 52 to enter the fluid circulation component 30 such that a closed fluid system is formed along fluid circulation component 30, heater component 40, and diagnostic bed 20.

In embodiments, any of the above-described components may be formed of any material or composition suitable for their intended purpose, for example, metallic, polymeric, and/or composite materials. In an exemplary embodiment, fluid delivery line 50 and/or fluid return line 52 may be formed of polyvinyl chloride (PVC). In embodiments, diagnostic device may comprise an MRI device that may be any suitable device having an electromagnetic element configured to generate one or more electromagnetic fields through the body of a subject to produce a resultant image of a portion of the body of the subject.

A control interface 60 may be provided in electrical communication with any of diagnostic device 10, diagnostic bed 20, fluid circulation component 30, or heater component 40 to control one or more operations thereof. As shown, control interface 60 may be in electrical communication with a portion of the body of the subject S, for example, via a thermal probe such as a thermometer or other sensory device applied to a portion of the subject S so that such signals may be incorporated into the control of any of diagnostic device 10, diagnostic bed 20, fluid circulation component 30, and heater component 40, for example, as biofeedback signals.

In the exemplary embodiment shown, user interface 60 may comprise an input device 62 such as a keyboard and/or mouse and a display 64 such as a computer monitor. Control interface 60 may comprise a processor (not shown) for running one or more computer-implementable processes. It will be understood that in embodiments, user interface may be, for example, a desktop computer, laptop computer, tablet computer, smartphone, PDA or other electronic device for communication with one or more components of diagnostic system 100.

Figure 2A:
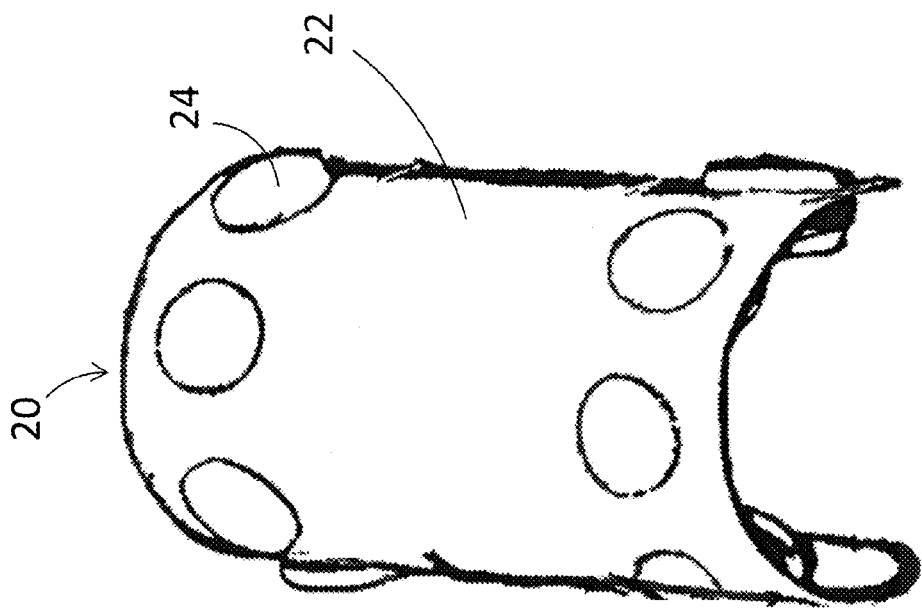
FIG. 2A is an elevated perspective view of the diagnostic bed of the diagnostic system of FIG. 1.
Figure 2B:
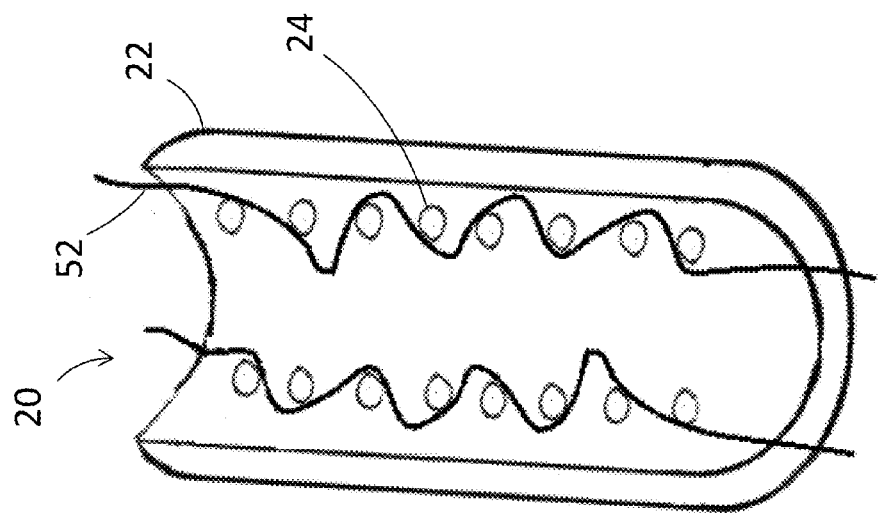
FIG. 2B is a bottom perspective view of the diagnostic bed of the diagnostic system of FIG. 1.

Turning now to FIGS. 2A and 2B, diagnostic bed 20 is shown in detail. Diagnostic bed 20 includes a frame 22 having a plurality of posts 24 protruding from opposing sides thereof. Frame 22, as shown, may be an elongate member defining a convex curvature in the orientation shown in FIG. 2A so that frame 22 has a half-shell profile. Accordingly, frame 22 may be configured to receive the body of one or more particular subjects that fit at least partially within the geometric boundaries defined by frame 22.

Posts 24, as shown, extend orthogonally from opposing surfaces of the frame 22 at radially and axially spaced locations therealong. In this manner, posts 24 present a variable topography along the surfaces of frame 22 so that one or both of fluid heating line 52 may be engaged, for example, wound, threaded, laced and/or looped therethrough to maintain the fluid return line 52 in position along the surface of diagnostic bed 20. In embodiments, one or more of posts 24 may define a widened portion thereof at a location spaced away from the surface of the frame 22 so that one or more of posts 24 present a flange for enhanced engagement of fluid return line 52. In embodiments, fluid return line 52 may extend along diagnostic bed 20 in any manner, for example, linear, diagonal, horizontal, curvate, serpentine, and/or overlapping, to name a few.

Figure 3A:
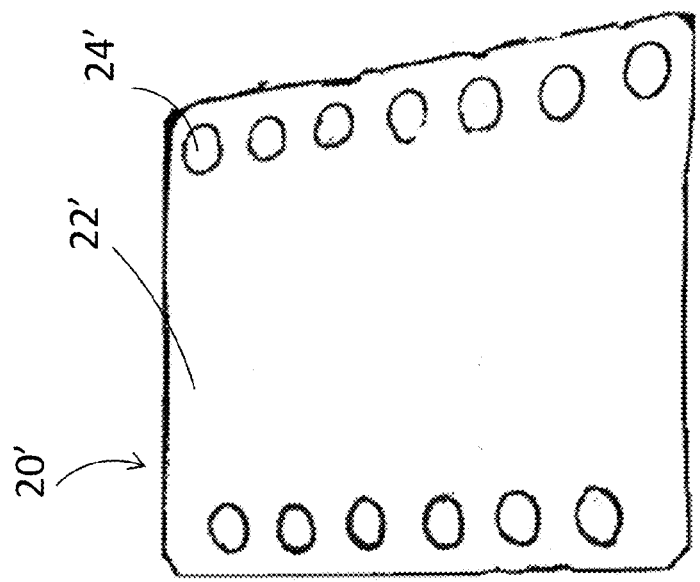
FIG. 3A is an elevated perspective view of the diagnostic bed of a diagnostic system according to an exemplary embodiment of the present disclosure.
Figure 3B:
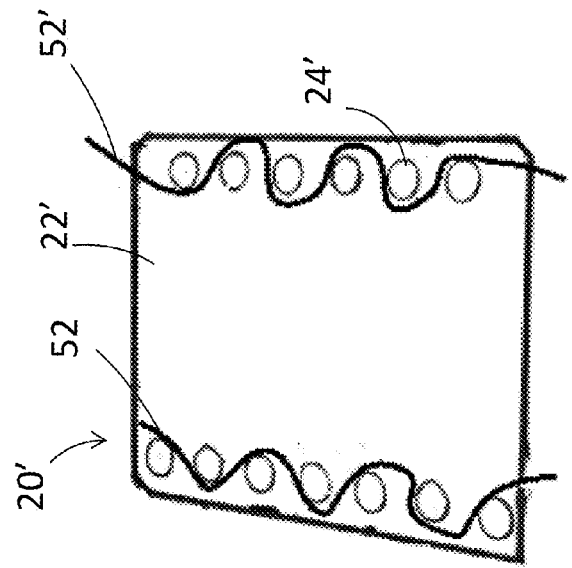
FIG. 3B is a bottom perspective view of the diagnostic bed shown in FIG. 3A.

Turning to FIGS. 3A and 3B, an exemplary embodiment of a diagnostic bed is generally designated 20'. Diagnostic bed 20' may include similar components to diagnostic bed 20 described above, however, diagnostic bed 20' has a frame 22' with a substantially flat planar profile. Accordingly, posts 24' protrude normally from one or more level surfaces of frame 22' for engagement with one or both fluid lines 50, 52. The flat configuration of frame 22' may provide an ideal support surface for a relatively large subject that would be frightened, uncomfortable, and/or constrained by the curvate profile of frame 22 described above.

Turning now to FIG. 4, an operational schematic diagram of diagnostic system 100 is shown, with a subject S disposed on the diagnostic bed 20 within the bore 12 of diagnostic device 10.

As shown, fluid circulation component 30 may comprise a radiator 32 adapted for the release of heat from a fluid so that an environment near or surrounding the fluid circulation component 30 may serve as a heat sink to absorb excess heat from the fluid. Fluid circulation component 30 further comprises a fluid reservoir 34 for storing an amount of fluid for use in diagnostic system 100, as well as a high-temperature (HT) fluid pump 36a, a low-temperature (LT) fluid pump 36b, and a pump controller 38 in electrical communication with pumps 36a, 36b for control thereof. In this manner, fluid circulation component 30 is configured to separately supply HT fluid and LT fluid therefrom. HT fluid and LT fluid may be supplied from separate sources, for example, municipal water lines or reservoirs, or may be adjusted to desired temperatures as described further herein.

Accordingly, and with additional reference to FIGS. 4 and 5, fluid delivery line 50 comprises a HT fluid line 50a and a separate LT fluid line 50b for delivery through heater component 40. In embodiments, HT fluid line 50a and LT fluid line 50b may be disposed within a common fluid line casing or wrapping, or may be physically separable.

As shown, heater component 40 comprises a heating element 42 and a mixing valve 44. Heating element 42 is configured to generate and transfer thermal energy to fluid flowing through the HT fluid line 50a such that the temperature of the fluid flowing through the HT fluid line 50a can be changed via under user control and/or automated control of heating element 42. Heating element 42 may be any suitable device for generating and transferring heat to a fluid medium, for example, an inductor or capacitor.

Mixing valve 44 is a three-way valve having an input for each of fluid from HT fluid line 50a and LT fluid line 50b, as well as an outlet to deliver fluid mixed from the HT fluid line 50a and LT fluid line 50b into the fluid delivery line 52.

As shown, fluid return line 52 extends near or along diagnostic bed 20 in the manner described above with respect to FIGS. 2A, 2B, 3A, and 3B. Accordingly, heat may be transferred from fluid return line 52 to the body of the subject S at a rate dependent upon the differential in temperature between the fluid in the delivery fluid line 50 and the body of the subject S. Other factors that may impact the transfer of heat between the fluids in the fluid return line 52 may include, for example, the thickness and/or thermal conduction process of either or both fluid return line 52 and diagnostic bed 20. In this manner, heat may be transferred between the subject S and the fluid in the fluid return line 52 by conduction (through the wall of fluid delivery line 50 and/or diagnostic bed 20), convection (for example, through air and/or another fluid disposed intermediate the subject S, diagnostic bed 20, and/or wall of fluid delivery line 50), and/or through radiation. After passing along the diagnostic bed 20, fluid return line 52 returns the mixed fluid to the radiator 32 of the fluid circulation component 30, as shown. This fluid may then be re-distributed through one or both of the HT fluid line 50a and LT fluid line 50b toward the heater component 40. It will be understood that control interface 60 provides a degree of control over a variety of aspects of operation of diagnostic system 100 in many combinations and separations thereof.

It will be understood that it is advantageous to dispose the mixing valve 44 near the diagnostic bed 20 so that heat losses along fluid return line 52 between the mixing valve 44 and diagnostic bed 20 are minimized. Further, by locating the mixing valve 44 near the diagnostic bed 20, the temperature of the fluid reaching the diagnostic bed 20 can be changed much more quickly than, for example, in systems requiring the entire fluid reservoir to change this temperature, or in systems where the mixing valve 44 is further from the diagnostic bed 20.

Turning now to FIGS. 6-10, diagnostic systems according to various exemplary embodiments of the present disclosure will be described. In particular, the following exemplary embodiments are directed to different configurations and/or variations of the fluid heat transfer system that facilitates the transfer of heat between a subject and the fluid flowing near or along the diagnostic bed. Accordingly, in the interest of brevity, similar components will be described with like reference numbers across different exemplary embodiments.

Figure 6:
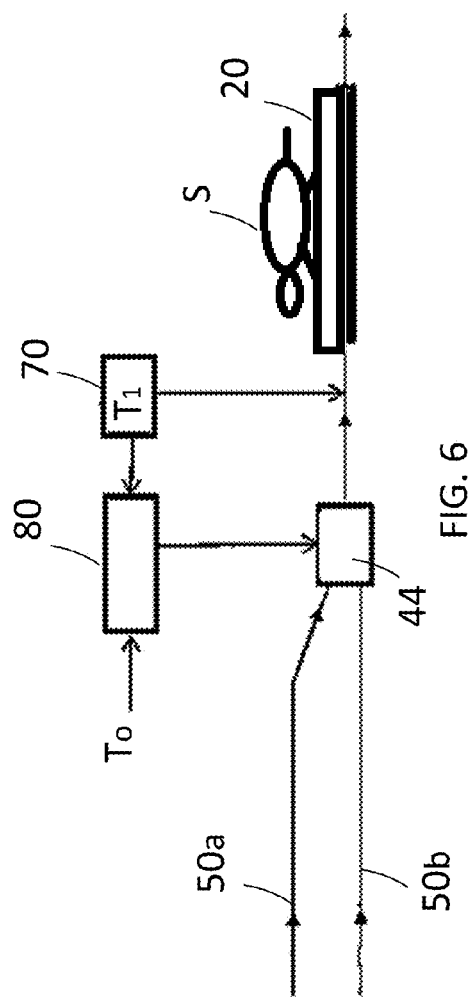
FIG. 6 is a schematic view of a portion of a diagnostic system according to an exemplary embodiment of the present disclosure.

With reference to FIG. 6, in one exemplary embodiment, the HT fluid line 50a and LT fluid line 50b are fluidly coupled via mixing valve 44 so that mixing valve 44 outputs a fluid mixture along fluid return line 52 to cause a desired change in a body temperature of the subject S. A sensor 70, for example, a thermocouple, thermometer, or thermistor, to name a few, is in communication with the fluid return line 52 and transmits the temperature $T_1$ of the mixed fluid in fluid return line 52 to a controller 80. Controller 80 may be a portion of control interface 60 described above, and is in electrical communication with sensor 70, control interface 60, and mixing valve 44. Accordingly, controller 80 is configured to compare the temperature $T_1$ of the mixed fluid against a designated target temperature $T_0$ that is input to the controller 80 by a user, for example, through control interface 60, and/or through an automated process of the diagnostic system. If the controller 80 determines that $T_1$ is different than $T_0$, i.e., the temperature $T_1$ of the mixed fluid being transported along diagnostic bed 20 is either higher or lower than the target temperature $T_0$, controller 80 can manipulate mixing valve 44 so that the temperature $T_1$ of the mixed fluid approaches equilibrium with the target temperature $T_0$. The controller 80 may manipulate mixing valve 44 for example, by moving an internal flap, ball, piston, radial collar, or other fluid flow restricting component to change a rate of flow of at least one of the fluid flowing from HT fluid line 50a and LT fluid line 50b to cause a change in the rate of heat transfer between the fluid in the fluid return line 52 and the subject S.

Figure 7:
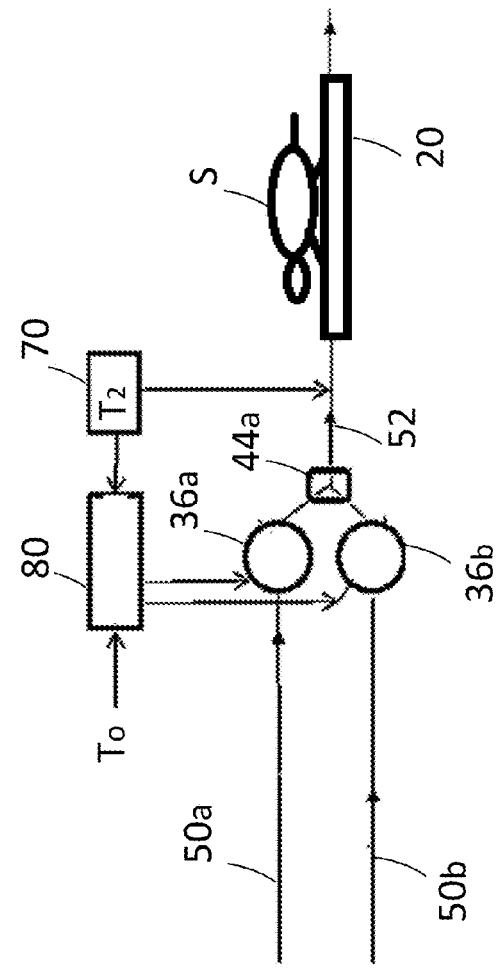
FIG. 7 is a schematic view of a portion of another diagnostic system according to an exemplary embodiment of the present disclosure.

With reference to FIG. 7, in an exemplary embodiment, the HT fluid line 50a and LT fluid line 50b are each fluidly coupled with a respective HT pump 36a and LT pump 36b that each feed into a mixing tee 44a so that mixing tee 44a forces mixing of the HT fluid and LT fluid so that a fluid mixture having an intermediate temperature $T_2$ is output to diagnostic bed 20 along fluid return line 52 to cause a desired change in a body temperature of the subject S. Sensor 70 is in communication with the fluid return line 52 and transmits the temperature $T_2$ of the mixed fluid in fluid return line 52 to the controller 80. Accordingly, controller 80 is configured to compare the temperature $T_2$ of the mixed fluid against a designated target temperature $T_0$ that is input to the controller 80 by a user, for example, through control interface 60, and/or through an automated process of the diagnostic system 100. If the controller 80 determines that $T_2$ is different than $T_0$, i.e., the temperature $T_2$ of the mixed fluid being transported along diagnostic bed 20 is either higher or lower than the target temperature $T_0$, controller 80 can change the output flow rate of one or both of HT fluid pump 36a and LT fluid pump 36b, so that the temperature $T_2$ of the mixed fluid approaches equilibrium with the target temperature $T_0$ to cause a change in the rate of heat transfer between the fluid in the fluid return line 52 and the subject S. By locating the mixing tee 44a in close proximity to the diagnostic bed 20, the temperature of the fluid reaching the diagnostic bed 20 will have an immediate impact on the temperature of the fluid reaching the diagnostic bed 20.

Figure 8:
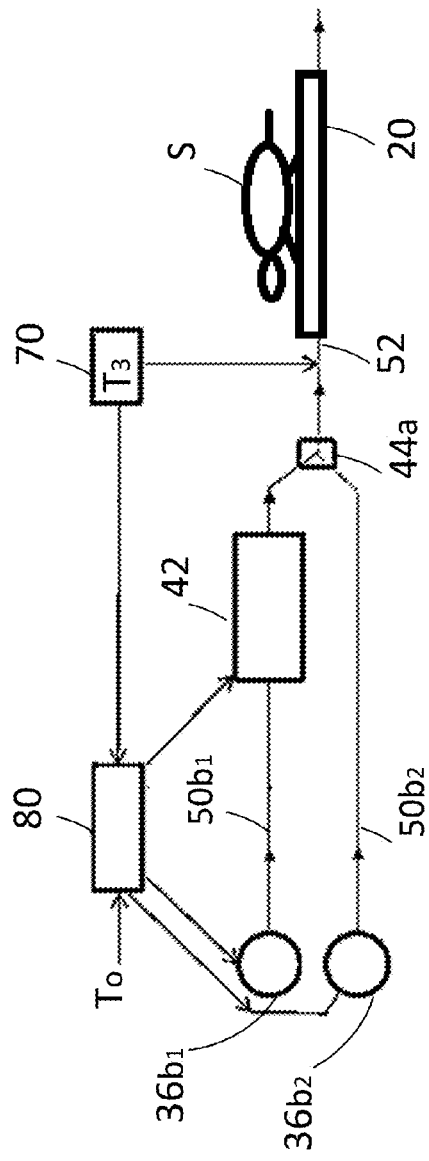
FIG. 8 is a schematic view of a portion of another diagnostic system according to an exemplary embodiment of the present disclosure.

With reference to FIG. 8, in one exemplary embodiment, a diagnostic system may be devoid of a dedicated HT fluid line and may instead incorporate a first LT fluid line $50b_1$ and a second LT fluid line $50b_2$ that are each are fluidly coupled with a respective first LT pump $36b_1$ and second LT pump $36b_2$ that feeds into mixing tee 44a so that mixing tee 44a outputs a fluid mixture toward diagnostic bed 20 along fluid return line 52. However, because first LT fluid line $50b_1$ and second LT fluid line $50b_2$ each carry fluid having a substantially similar temperature $T_{L1}$ and $T_{L2}$, heater element 42 is disposed along first LT fluid line $50b_1$ to apply heat to fluid flowing therethrough and raise the fluid temperature from $T_{L1}$ to $T_H$. Since the temperature of the fluid in the line is controlled by the heater 42 rather than the temperature of the reservoir 34, the temperature can change more rapidly. Accordingly, as the fluid exiting heater element 42 along first LT fluid line $50b_1$ having fluid temperature $T_H$ enters the mixing tee 44a along with second LT fluid line $50b_2$ having fluid temperature $T_{L2}$ shown, mixing tee 44a produces a mixed fluid output having a desired intermediate fluid temperature $T_3$. Controller 80 is configured to compare the temperature $T_3$ of the mixed fluid against a designated target temperature $T_0$ that is input to the controller 80 by a user, for example, through control interface 60, and/or through an automated process of the diagnostic system. If the controller 80 determines that $T_3$ is different than $T_0$, i.e., the temperature $T_3$ of the mixed fluid being transported along diagnostic bed 20 is either higher or lower than the target temperature $T_0$, controller 80 can change the output flow rate of one or both of first LT fluid pump $36b_1$ and second LT fluid pump $36b_2$, so that the temperature $T_3$ of the mixed fluid approaches equilibrium with the target temperature $T_0$ to cause a change in the rate of heat transfer between the fluid in the fluid return line 52 and the subject S. Again, by locating the mixing tee 44a in close proximity to the diagnostic bed 20, the temperature of the fluid reaching the diagnostic bed 20 will have an immediate impact to rapidly changing a body temperature of the subject S.

Figure 9:
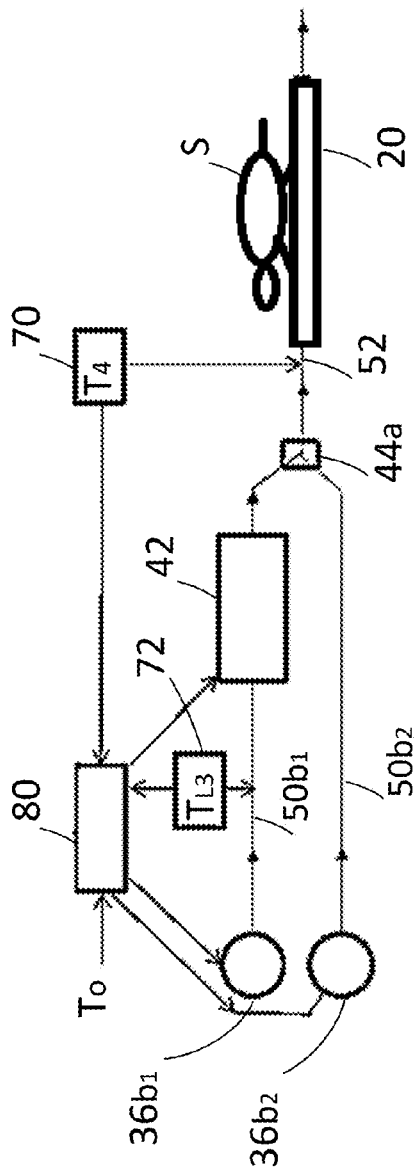
FIG. 9 is a schematic view of a portion of another diagnostic system according to an exemplary embodiment of the present disclosure.

Turning to FIG. 9, an exemplary embodiment of a configuration for a diagnostic system similar to FIG. 8 described above is shown, with an additional sensor 72 providing the temperature $T_{L1}$ of the first LT fluid line $50b_1$ prior to passing through the heater element 42 Accordingly, the controller 80 may cause an increase in the amount of heat transferred from heater element 42 into the fluid traveling therethrough along first LT fluid line $50b_1$ to cause a subsequent increase in the rate of heat transfer between the fluid in the fluid return line 52 and the subject S. Accordingly, this configuration of control between the fluid in the fluid return line 52 and the subject S may be a function of the amount of energy supplied to heater element 42 in addition to or alternative to the output of one or both of first LT fluid pump $36b_1$ and second LT fluid pump $36b_2$.

Figure 10:
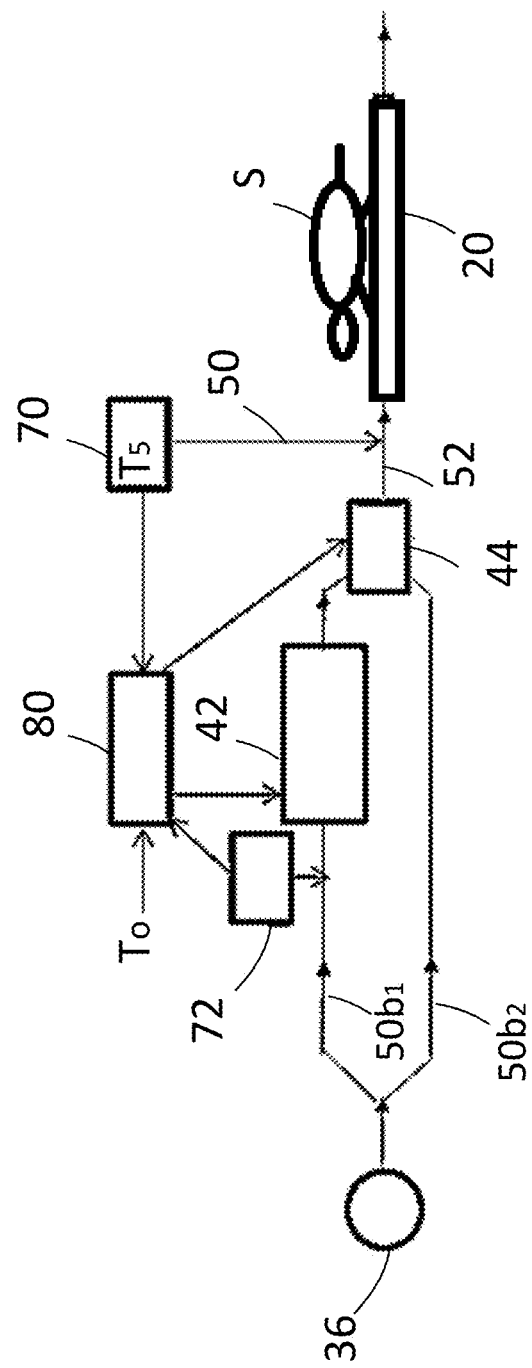
FIG. 10 is a schematic view of a portion of another diagnostic system according to an exemplary embodiment of the present disclosure.

Turning to FIG. 10, an exemplary embodiment of a configuration for a diagnostic system similar to FIG. 9 described above is shown, with a single LT fluid pump 36 driving fluid simultaneously through first LT fluid line $50b_1$ toward heater element 42 and through second LT fluid line $50b_2$ toward mixing valve 44 as shown. Accordingly, a fluid partition, valve, or other flow divider may be provided to separate the first LT fluid line $50b_1$ and second LT fluid line $50b_2$ downstream of LT fluid pump 36. Sensor 72 provides a temperature $T_{L3}$ of the first LT fluid line $50b_1$ prior to passing through the heater element 42. Accordingly, the controller 80 may cause an increase in the amount of heat transferred from heater element 42 into the fluid traveling along first LT fluid line $50b_1$ to cause a subsequent increase in the rate of heat transfer between the fluid in the fluid return line 52 and the subject S. Accordingly, this configuration of control between the fluid in the fluid return line 52 and the subject S may be a function of the output of the single LT fluid pump 36a and in addition to or alternative to the amount of energy supplied to heater element 42.

In each embodiment, the location of the final mix and final adjustment of the temperature of the water or other fluid is in close proximity to the diagnostic bed 20. This provides the ability to make rapid changes to the temperature of the diagnostic bed 20 and the test animal S.

While this invention has been described in conjunction with the embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A diagnostic system, comprising:
   an MRI device and an associated bed for supporting a portion of a subject during a diagnostic procedure;
   a fluid heat transfer system, comprising:
      a fluid circulation component;
      a heater component including a heater element and a mixing valve, the fluid circulation component fluidly coupled to the heater component so that a fluid can be pumped from the fluid circulation component to the heater component; and
      a fluid line extending from the heater to the fluid circulation component, the mixing valve of the heater positioned near the bed so that heat can be rapidly transferred through the fluid line to alter a body temperature of the subject.

2. The diagnostic system of claim 1, wherein the mixing valve comprises an inlet for the fluid at a first temperature and an inlet for the fluid at a second, higher temperature.

3. The diagnostic system of claim 2, wherein the mixing valve comprises an outlet for the fluid at a temperature intermediate the first temperature and second temperature.

4. The diagnostic system of claim 1, wherein the bed comprises a frame and a plurality of protrusions extending therefrom.

5. The diagnostic system of claim 1, wherein the fluid line is configured to interengage one or more protrusion of the plurality of protrusions to maintain the fluid line in position near the bed.

6. The diagnostic system of claim 1, wherein the fluid circulation component comprises a pump.

7. The diagnostic system of claim 1, further comprising a control interface electrically coupled with one or more of fluid circulation component and heater component.

8. The diagnostic system of claim 7, wherein the control interface is electrically coupled with the mixing valve.

9. The diagnostic system of claim 8, wherein the control interface can cause a flow rate through one of a first inlet and a second inlet of the mixing valve to change.

10. A diagnostic system, comprising:
    a bed configured for use with an MRI device and to support a portion of a subject during a diagnostic procedure; and
    a fluid heat transfer system, comprising:
       a first fluid line fluidly coupled with a heating element;
       a second fluid line;
       a mixing valve disposed downstream of the heating element and having a first fluid inlet corresponding to the first fluid line and a second fluid inlet corresponding to the second fluid line, the mixing valve having an outlet for a mixed fluid having a temperature higher than a temperature of fluid in the second fluid line; and
       a third fluid line extending away from the mixing valve, the mixing valve positioned near the bed such that the mixed fluid rapidly transfers heat from the third fluid line to a subject on the bed.

11. The diagnostic system of claim 10, wherein a first fluid pump is fluidly coupled with the first fluid line.

12. The diagnostic system of claim 11, wherein a second fluid pump is fluidly coupled with the second fluid line.

13. The diagnostic system of claim 11, further comprising a controller operably coupled with each of the first fluid pump and the second fluid pump.

14. The diagnostic system of claim 10, further comprising a controller operably coupled with the heating element.

15. The diagnostic system of claim 14, wherein a thermal sensor is disposed downstream of the mixing valve and electrically coupled with the controller such that the controller controls the transfer of heat from the heating element into fluid therealong.

16. The diagnostic system of claim 15, wherein another thermal sensor is disposed upstream of the mixing valve and in electrical communication with the controller so that the controller can determine a difference in the temperature at the thermal sensor with the temperature at the another thermal sensor.

* * * * *